United States Patent [19]

Sacks et al.

[11] Patent Number: 5,141,534
[45] Date of Patent: Aug. 25, 1992

[54] SAMPLE COLLECTION AND INLET SYSTEMS FOR GAS CHROMATOGRAPHY APPARATUS

[75] Inventors: Richard D. Sacks; Mark A. Klemp; Christine L. Rankin, all of Ann Arbor, Mich.

[73] Assignee: The Regents of the University of Michigan, Ann Arbor, Mich.

[21] Appl. No.: 717,356

[22] Filed: Jun. 18, 1991

Related U.S. Application Data

[63] Continuation-in-part of Ser. No. 590,174, Sep. 28, 1990, Pat. No. 5,096,471.

[51] Int. Cl.$^5$ .............................................. B01D 15/08
[52] U.S. Cl. ....................................... 55/197; 55/267; 55/386
[58] Field of Search .................... 55/67, 197, 208, 267, 55/269, 386

[56] References Cited

U.S. PATENT DOCUMENTS

| | | | |
|---|---|---|---|
| 3,111,835 | 11/1963 | Jenkins | 73/23 |
| 3,220,164 | 11/1965 | Golay | 73/23.42 X |
| 3,496,702 | 2/1970 | Carel et al. | 55/67 |
| 3,550,428 | 12/1970 | Mator et al. | 73/23.36 |
| 3,735,565 | 5/1973 | Gilby et al. | 55/197 |
| 3,948,602 | 4/1976 | Solomon | 55/67 X |
| 4,035,168 | 7/1977 | Jennings | 55/197 X |
| 4,038,053 | 7/1977 | Gday | 55/67 X |
| 4,477,266 | 10/1984 | Yang et al. | 55/67 |
| 4,805,441 | 2/1989 | Sides et al. | 73/23.1 |
| 4,863,871 | 9/1989 | Munari et al. | 436/161 |
| 4,923,486 | 5/1990 | Rubey | 55/67 |
| 4,962,042 | 10/1990 | Morabito et al. | 55/197 X |

OTHER PUBLICATIONS

"Sample Enrichment in High Speed Narrow Bore Capillary Gas Chromatography", Van Es et al., J. of High Resolution Chrom. & Chrom, Communications, vol. 11, Dec. 1988, pp. 852–857.
"Rapid Evaporation of Condensed Gas Chromatographic Fractions", Hopkins et al., J. of Chromatography, 158 (1978) 465–469.
B. A. Ewels and R. D. Sacks, 1985, "Electrically Heated Cold Trap Inlet System for High-Speed Gas Chromatography", Analytical Chemistry, 57, 2774–2779.
Lanning, Sacks, Mouradian, Levine, Foulke, "Electrically Heated Cold Trap Inlet System for Computer-Controlled Controlled High-Speed Gas Chromatography", Anal. Chem. 1988, 60, 1994–1996.
S. Levine, R. Sacks, Jul. 1, 1986–Jun. 30, 1988, "Fast-GC for Industrial Hygiene Monitoring/Analysis", U. of Michigan, Grant No. 86-863-J1.

*Primary Examiner*—Robert Spitzer
*Attorney, Agent, or Firm*—Harness, Dickey & Pierce

[57] ABSTRACT

A gas chromatography system of the type incorporating a thermal focusing chamber for introducing a sample into a column for separation and analysis. The system of the present invention provides benefits in terms of reducing memory effect of one analysis being influenced by prior experiments, a reduction in system dead volume which leads to broadening of peaks produced on the chromatogram and artifacts caused by sample decomposition. These advantages are achieved principally through a novel fluid circuit in which the sample is trapped onto the column by trapping it at the end of the thermal focusing chamber closest to the column. This feature has the effect of eliminating the necessity of the sample residing in the heated focusing chamber for a period giving rise to sample decomposition. This system further avoids the necessity of passing the inlet flow through mechanical valves which also contributes to memory effect. This system further has the benefit of enabling sampling of sources at various pressures including ambient pressure as an air quality sensing probe. An alternative embodiment is a simplified system for enabling ambient pressure source monitoring without mechanical valves in the sample flow path.

20 Claims, 4 Drawing Sheets

SAMPLE COLLECTION AND INLET SYSTEMS FOR GAS CHROMATOGRAPHY APPARATUS

CROSS REFERENCE TO RELATED APPLICATIONS

This application is a continuation-in-part of co-pending U.S. patent application Ser. No. 590,174 filed on Sep. 28, 1990 entitled "Gas Chromatography System and Method", now U.S. Pat. No. 5,096,471 which is hereby incorporated by reference.

BACKGROUND AND SUMMARY OF THE INVENTION

This invention relates to apparatuses for gas chromatography and particularly to novel sample collection and inlet systems for such devices.

Gas chromatography is a widely employed technique for the separation and analysis of complex mixtures of volatile organic and inorganic compounds. The analyte mixture is separated into its components by eluting them from a column having a sorbent by means of a moving gas.

Gas chromatography procedures can be classified into two major divisions; gas-liquid chromatography, and gas-solid chromatography. Gas-liquid chromatography is presently the most widely used type and incorporates a non-volatile liquid sorbent coated as a thin layer on an inner support structure, generally the inside surface of a capillary tube. The moving gas phase, called the carrier gas, flows through the chromatography column. The analyte partitions itself between the moving gas phase and the sorbent and moves through the column at a rate dependent upon the partition coefficient or solubility of the analyte components. The analyte is introduced at the entrance end of a column within the moving carrier gas stream. The components making up the analyte become separated along the column and escape from the exit end of the column at intervals and in concentrations characteristic of the properties of the analyte components. A detector, for example, a thermal conductivity detector or a flame ionization detector (FID) at the exit end of the column responds to the presence of the analyte components. Upon combustion of the eluted material at a FID, charged species are formed in the flame. The flame characteristics are monitored through a biased ion detector which, along with associated electronics, produces a chromatogram which is a time versus magnitude trace of the detector output. The trace for complex mixtures includes numerous peaks of varying intensity. Since individual constituents of the analyte produce peaks at characteristic times and whose magnitude is a function of their concentration, much information is gained through an evaluation of the chromatogram.

Gas chromatography systems of the type generally described above are in widespread use today. Although present systems provide excellent performance and utility, this invention seeks to provide a number of improvements to existing apparatuses. Various approaches are presently used for introducing a sample into the separation column. In one general type of gas chromatography systems, a thermal focusing chamber or cold trap is employed. The cold trap is typically a vessel containing a cold gas such as nitrogen having a capillary sample tube passing through it which conducts the analyte. By exposing incoming analyte to the low temperatures within a cold trap, the analyte components condense on the capillary tube. When it is desired to inject a sample into the column for separation, the temperature of the sample tube passing through the cold trap is increased rapidly thus vaporizing the sample. The carrier gas stream which continually flows through the trap then injects the analyte into the column for separation.

In a typical gas chromatography system of the type employing a thermal focusing chamber, during the trapping mode of operation, the incoming analyte is trapped at the inlet end of the cold trap sample tube (i.e. in the direction of carrier gas flow during injection). After heating the cold trap sample tube, the sample components must traverse the entire length of the sample tube before introduction into the column. The sample flow circuit regions between where the component is vaporized and the beginning of the column constitutes system "dead volume" which is undesirable since it results in broadening of the injected analyte in terms of the time duration over which it is presented at the inlet end of the column. Dead volume adversely affects system resolution and efficiency.

Today there is increased emphasis toward so called "fast gas chromatography" or "fast GC". Applications include process stream monitoring, environmental monitoring, and engine exhaust gas analysis. Ideally such systems would be able to perform an analysis within several seconds which previously took several minutes or more. Increasing the speed of analysis can be achieved by providing a relatively short separation column or by using other techniques for causing components of interest to traverse the column quickly. In order to provide useful information, the individual analyte components must elute separately at the detector, thus producing distinct peaks. As the length of time that the sample is injected at the inlet end of the column increases, the peaks produced by elution of the components tend to broaden, smear and overlap. It is, therefore, essential that a narrow sample "plug" be presented at the column during injection in order to provide gas chromatography evaluation in a small period of time. It is for this reason that the dead volume associated with conventional cold trap type gas chromatography systems is a disadvantage.

In gas chromatography systems of the type described previously which employ a thermal focusing chamber or cold trap, it must be understood that the entire length of the cold trap sample tube cannot be maintained ideally at a uniform constant temperature, either during the collection or injection modes. In fact, a temperature gradient exists at the inlet and outlet ends of the cold trap capillary tube. Since during the collection mode of operation, the analyte condenses at near the inlet end of the capillary tube (in terms of the direction of flow of carrier gas during injection), it is necessary to insure that that region is sufficiently heated to vaporize all of the components of interest of the mixture during the injection step. This requirement leads to some portions of the cold trap sample tube being heated to a significantly higher temperature than is necessary to vaporize the sample collected at the inlet end of the sample tube. Furthermore, the analyte is exposed to the excessive temperatures for the length of time necessary to conduct them entirely through the focussing chamber. These excessive temperatures and the significant "residence time" in the sample tube have been related to decomposition of analyte components. Accordingly, instead of components in their natural state being ejected from the column, these components become fragmented into parts of the initial molecule. Such decomposition of the sample significantly complicates analysis and can render the generated chromatogram of little value in certain types of evaluation.

Furthermore, in many conventional gas chromatography systems, mechanical valves are used to control the inlet flow of analytes. Valves are available which are especially designed for gas chromatography systems and are generally micro-pneumatic type valves which have a relatively small dead volume. Despite the advanced state of the design of present valves, they nonetheless contribute to dead volume and have a tendency to retain a small portion of a prior sample which becomes mixed with the following sample during the next actuation of the valve. Accordingly, prior samples can influence subsequent samples, creating an undesirable artifact termed a "memory effect".

Mechanical valves which are used in many present gas chromatography systems are used for conducting the sample flow. When using valves in this manner, inevitable sample loss occurs as the sample coats internal surfaces within the valves. Another disadvantage of such valves in the sample flow path is the fact that they can contaminate the sample with lubricants or other coatings which are present in the valve.

The first described embodiments of a gas chromatography system in accordance with the present invention improves over present devices with respect to each of the previously described areas. A significant reduction in inlet system dead volume and decomposition of the analyte during injection is achieved principally through a gas chromatography circuit which introduces the sample into the cold trap sample tube at the end which is closest to the separation column (i.e. the outlet end for the carrier gas during the injection mode). In other words, the system utilizes a reverse flow direction through the cold trap during the collection mode as compared with injection. Since the analyte is trapped directly adjacent the separation column, the retained volume between the point of collection and the column is minimized, thus reducing system dead volume. This trapping approach also provides another significant benefit; namely, that upon injection the analyte components are only heated to the degree necessary to vaporize them whereupon they exit the cold trap without passing through a positive temperature gradient, reducing decomposition. In fact, these inventors have found that satisfactory injection can be achieved without increasing the temperature of the cold trap sample tube to the level necessary with prior art systems, enabling the use of lower capacity power supplies. Perhaps more importantly, the lower injection temperatures significantly enhances the operational longevity of the cold trap sample tube which is subject to significant temperature extremes and gradients leading to mechanical stresses and eventual failure.

Another benefit of the system according to this invention is that the sample is introduced into the system and injected into the column without ever passing through mechanical valves. This advantage leads to virtual elimination of the memory effect and contamination discussed previously. The system according to the present invention is further adaptable for evaluating samples introduced at a broad range of ambient pressures for use as an air quality "sniffing" probe or with positive pressure inlet sources.

A gas chromatography system in accordance with a second embodiment of this invention does not provide the feature of trapping analyte at the outlet end of the cold trap sample tube. However, it does provide the features of eliminating mechanical valves in the sample flow path and in fact, requires only a single valve to control its operation. Thus the problems associated with wear and failure of mechanical valves are minimized in the system of the second embodiment of this invention. The system of the second embodiment is furthermore vastly simplified in terms of the number of components and connections which provides inherent advantages in terms of reliability.

Both the embodiments of this invention provide the additional benefit that the inlet system is continually flushed with carrier gas when collection is not taking place, thus further reducing the likelihood of the memory effect discussed previously.

Additional benefits and advantages of the present invention will become apparent to those skilled in the art to which this invention relates from the subsequent description of the preferred embodiments and the appended claims, taken in conjunction with the accompanying drawings.

DETAILED DESCRIPTION OF THE INVENTION

Figure 1:
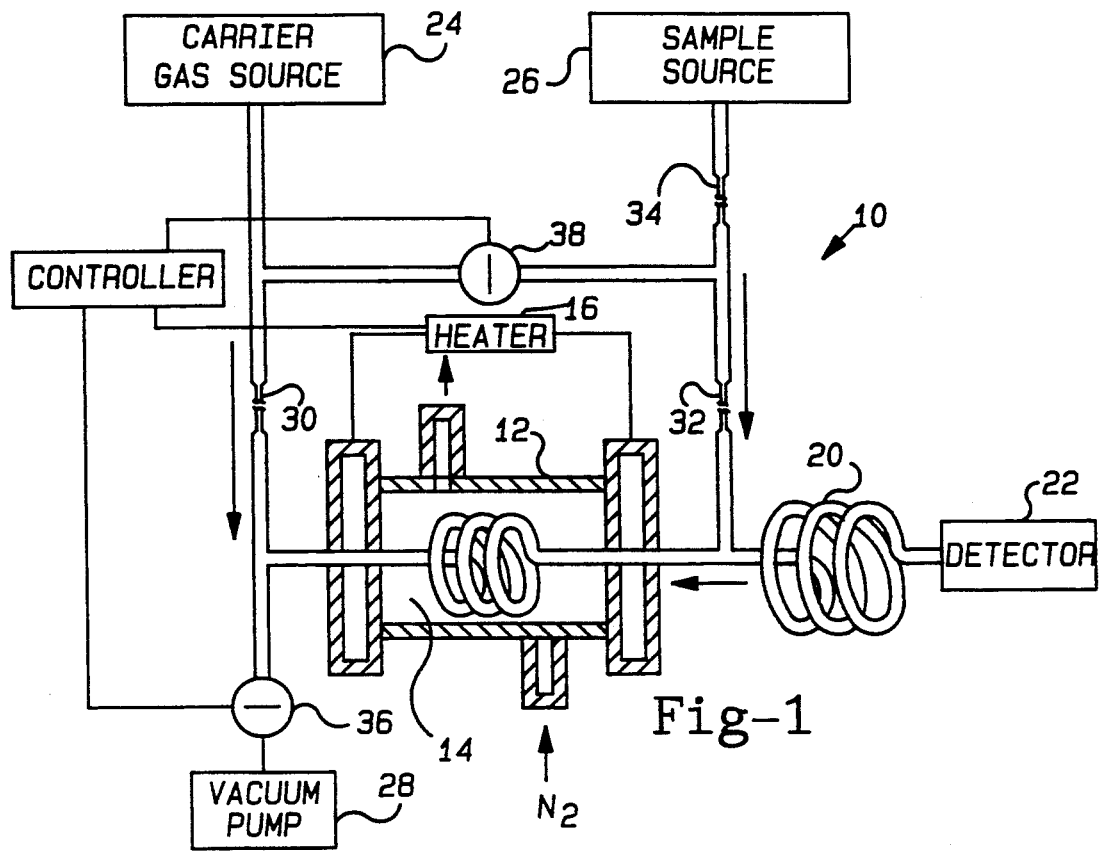
FIG. 1 is a schematic diagram of a gas chromatography system according to a first embodiment of this invention showing the direction of fluid flow when the system is in the collection mode.
Figure 2:
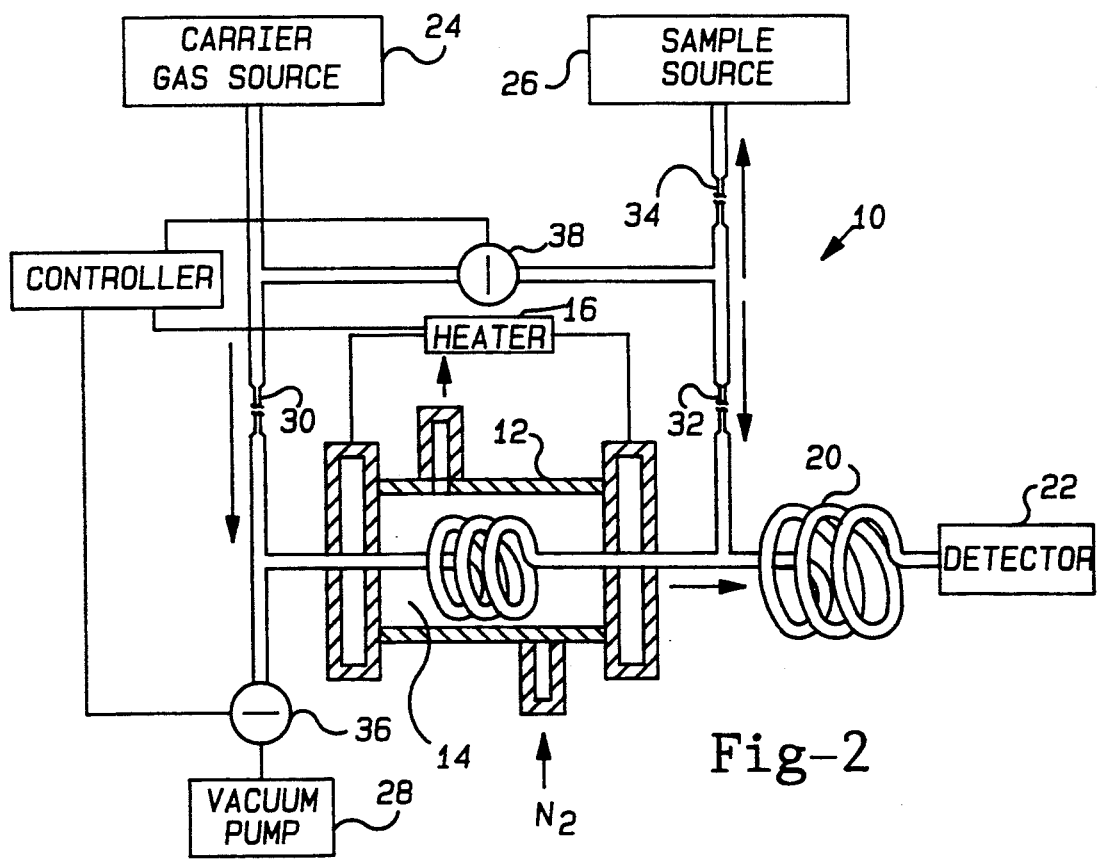
FIG. 2 is a schematic diagram similar to FIG. 1 except showing the fluid flow directions when the system is in the injection mode.
Figure 3:
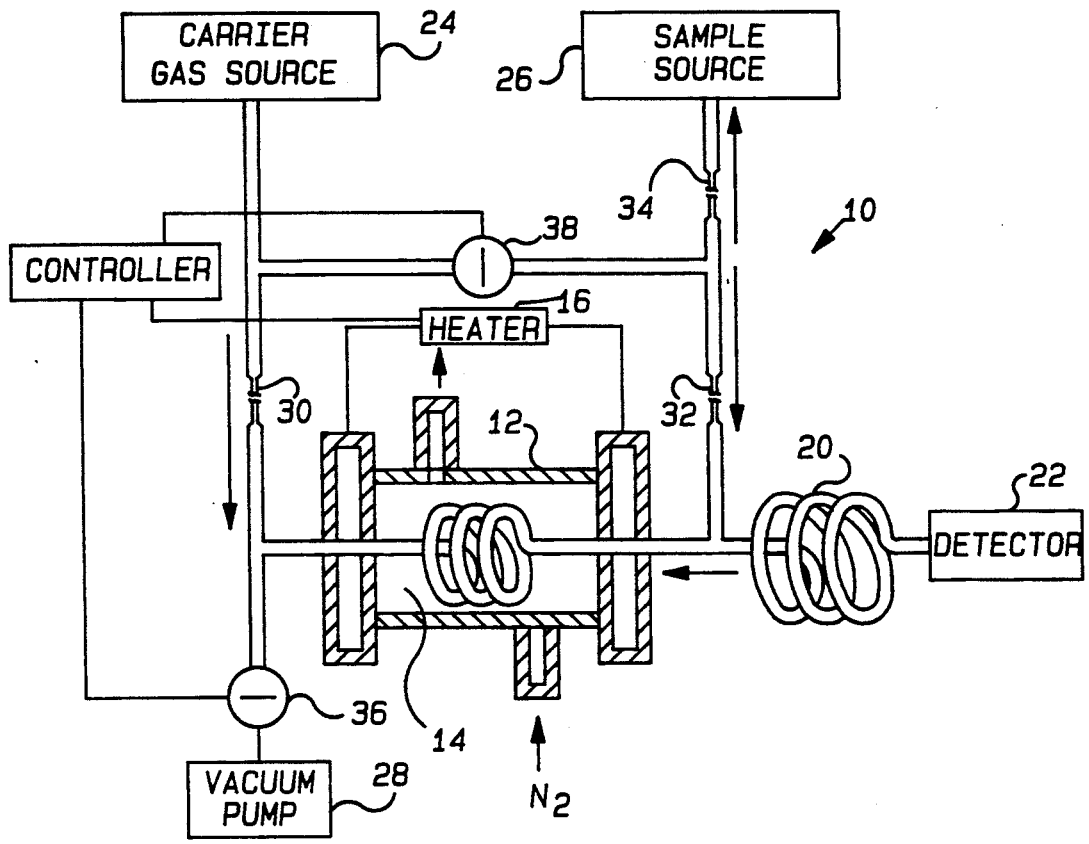
FIG. 3 is a schematic diagram similar to FIG. 1 except showing the fluid flow directions in a backflush mode.

FIGS. 1, 2, and 3 provide a schematic diagram of a gas chromatography system in accordance with a first embodiment of this invention which is generally designated by reference number 10. As shown, gas chromatography system 10 includes a thermal focusing chamber or cold trap 12 having inlets and outlets for conducting the flow of a cryogenic gas such as nitrogen. A short length of metal capillary sample tube 14 passes through chamber 12 and conducts the analyte through the chamber. Heater circuit 16 is connected to metal sample tube 14 via a pair of conductive block or soldered connections and provides a short duration, high current pulse which causes extremely rapid heating of the sample tube. One such heater circuit which can be employed in conjunction with this invention is a multi-stage capacitive discharge circuit such as described in the parent of this application. Sample tube 14 is connected to gas chromatography separation column 20 which is preferably a fused silica capillary tube. The opposite end of column 20 is connected to detector 22 which may be a flame ionization detector (FID). Carrier gas source 24 provides the source of a carrier gas such as hydrogen or helium and communicates with sample tube 14 through a conduit branch. Sample source 26 provides a sample at a pressure which is less than that of carrier gas source 24 and may be at ambient pressure or below and is connected between sample tube 14 and column 20 through another conduit branch. Vacuum pump 28 communicating with the inlet end of sample tube 14 provides a low pressure at about a few Torr. As shown, various pneumatic restrictors 30, 32, and 34 are provided which are comprised of varying lengths of capillary tube which are used to control the flow rates of fluids through the various flow paths.

A pair of valves 36 and 38 are provided which are preferably pneumatically or electrically controlled on/-off valves. As shown, valve 38 controls the flow of fluids between the carrier gas and sample flow paths, and valve 36 exposes the inlet end of sample tube 14 to vacuum pump 28. In an alternate embodiment (not shown) valve 36 could be eliminated in favor of a vacuum pump 28 which inherently performs the function of valve 36 when not energized. Operation of valves 36 and 38, heater 16, and vacuum pump 28 is coordinated by controller 40.

Now with reference to FIGS. 1, 2 and 3, the operation of system 10 will be described. The arrows in the figures indicate the direction of fluid flow in the various modes of operation. FIG. 1 represents system 10 in a collection mode of operation. In this mode, valve 36 is opened and valve 38 is closed. By having valve 36 open, vacuum pump 28 serves as the lowest pressure point for the three separate flow paths originating at carrier gas source 24, sample source 26 and detector 22. Thus, fluids flow through all the flow paths toward vacuum pump 28. During this mode of operation, thermal focusing chamber 12 is at a low temperature and, therefore, the sample condenses on sample tube 14 as it is being introduced into the chamber at its end closest to column 20. A small amount of carrier gas is being continually vented at vacuum pump 28.

After a sample collection interval of, for example, several seconds, valve 38 is opened and valve 36 is closed which corresponds to the injection mode of operation. Simultaneously, a heating pulse is provided by heater circuit 16 to vaporize the collected sample. In this mode, detector 22 which is exposed to atmosphere constitutes the lowest pressure point of the system. The main flow of carrier gas in this mode is through restrictor 30 and then through sample tube 14 and into column 20. A secondary forward flow of carrier gas originates from source 24 and travels through valve 38, restrictor 32 and then to column 20. The relative flow rates through these two paths are determined by the characteristics of restrictors 30 and 32. It is also significant that during this mode of operation a reverse flow occurs through restrictor 34 which has the effect of purging the conduit and that restrictor, thus eliminating the remnants of prior samples from influencing subsequent evaluations. It should further be noted that the flow of carrier gas through restrictor 32 dilutes the sample being introduced from thermal focusing chamber 12. Accordingly, it is important to limit the flow rate through this pathway. As mentioned previously, during the injection mode, the sample which has collected at the outlet side of sample tube 14 is directly imputed into column 20 without passing through the remainder of the sample tube 14.

FIG. 3 illustrates gas chromatography system 10 during a backflush mode of operation in which both valves 36 and 38 are opened. In this mode, both carrier gas source 24 and detector 22 serve as high pressure points for the system whereas vacuum pump 28 defines the low pressure point. Any analyte components remaining in column 20 will be redirected back into thermal focusing chamber 12 where they can be vented through vacuum pump 28 if the trap is maintained at a high temperature or refocused if the trap is maintained at a cold temperature. Accordingly, this system can be used to provide a retrapping and reinjection mode as described in the parent of this application. Since valve 38 is open there remains a purge flow from carrier gas source 24 to the sample source 26 (which is at a lower pressure than the carrier gas source). Therefore, the system is not subject to contamination from the sample inlet during backflushing.

In order to provide the desired fluid flow directions and relative flow rates, it will be necessary to select the value of restrictors 30, 32, and 34 in accordance with the specific requirements of a particular application. In some instances, separate restrictor elements may be unnecessary due to the inherent flow restriction characteristics of various conduits used to form the system.

In an experimental prototype of the first embodiment, column 20 comprises a 4.0 meter long, 0.25 mm. i.d. fused silica capillary tube within a 0.25 microns thick methyl silicone stationary phase. Each of the restrictors were formed from 0.1 mm. fused silica deactivated capillary tubes with restrictors 30, 32 and 34 having lengths of 25 cm., 60 cm. and 25 cm., respectively. Valves 36 and 38 where SGE pneumatic on-off valves in "L" configuration with 50 mm. stems. Valves 36 and 38 where actuated by Valcor Model H55P18DIA solenoid valves and a gas source of about 60 PSI. The vacuum pump 28 used was a Central Scientific HYVAC 7, two-stage pump.

As briefly described previously, gas chromatography system 10 possesses a number of significant advantages. The decomposition of sample attributed to vaporization in a thermal focusing chamber is significantly reduced from earlier systems since the sample is trapped at the downstream end of sample tube 14 and thus has less of the sample tube to travel through before it is injected into column 20 and it is, therefore, exposed less to the high temperature in the sample tube. Moreover, the maximum temperature the sample is exposed to is reduced. This downstream trapping also significantly reduces the systems dead volume which leads to increased efficiency and separation. Sample components are more easily injected to separation column 20, which reduces the required temperature for injection which in turn will lengthen the service life of sample tube 14. Neither valve 36 nor 38 are in the flow path of the sample components thus substantially minimizing the memory effect and sample contamination. In addition, the inlet system is continually purged when sample collection is not taking place which further minimizes the memory effect. And finally, since system 10 pulls a sample from source 26 using vacuum pump 28, the system is applicable to a wide range of inlet environments including direct air monitoring.

Figure 4:
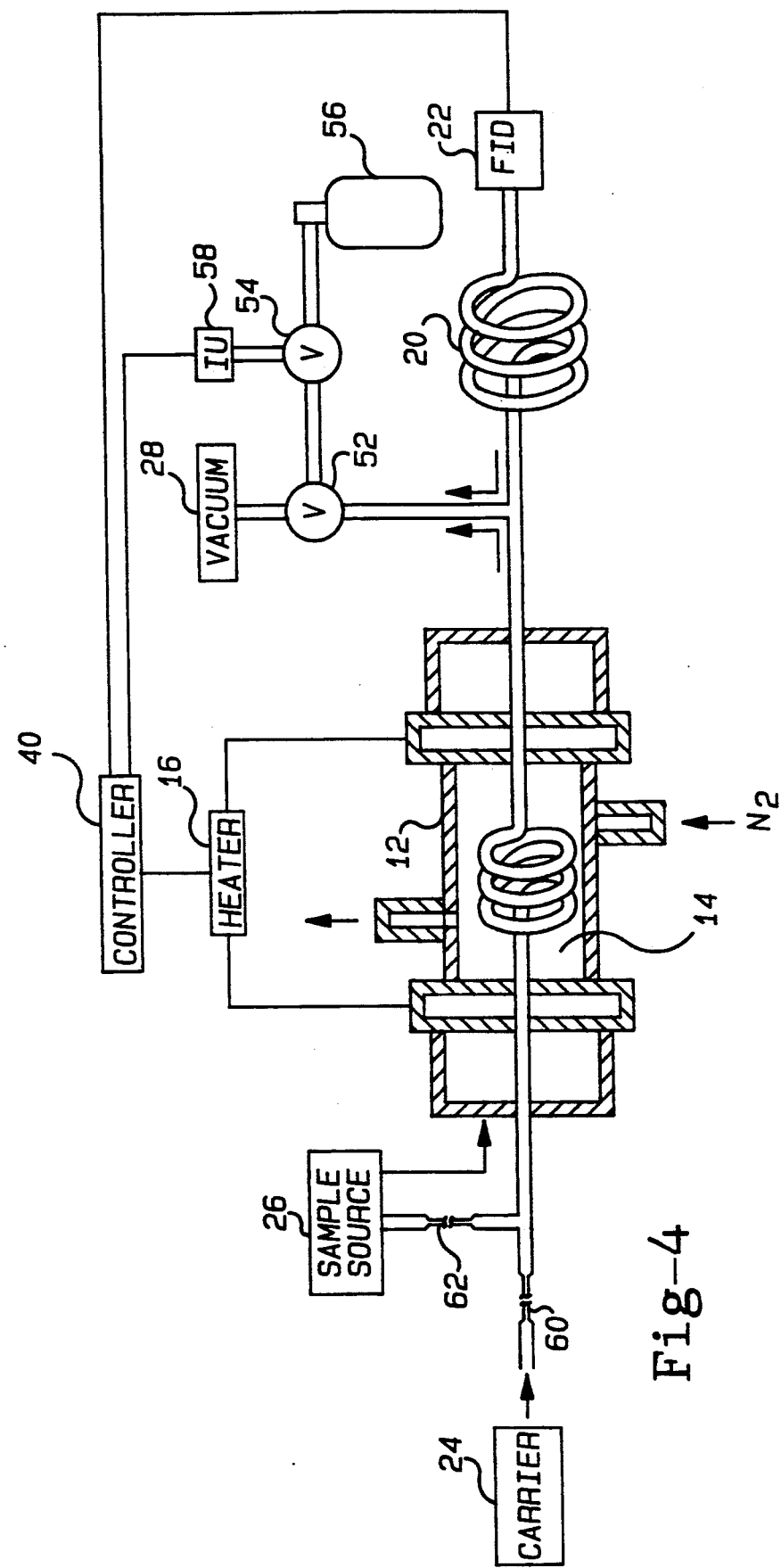
FIG. 4 is a schematic diagram of a gas chromatography system according to a second embodiment of this invention showing the direction of fluid flow when the system is in the collection mode.

With reference to FIG. 4, second embodiment of a gas chromatography device in accordance with this invention is shown which is generally designated by reference number 50. Gas chromatography system 50 has a number of components which are identical to that of system 10 and are accordingly identified by like reference numbers. Gas chromatography system 50 does not feature the reverse flow characteristic described in conjunction with the prior embodiment. The system does, however, provide a simplified apparatus which is particularly adapted for air quality monitoring as a "sniffing" probe. System 50 like the previous embodiment features an elimination of mechanical valves that are directly in the flow circuit through which a sample is introduced. As mentioned in conjunction with the first embodiment, this is related to a reduction in system memory effect, contamination, and loss of sample attributed to such valves. System 50 also features an efficient and thorough backflushing flow condition like the earlier embodiment.

As shown, system 50 utilizes vacuum pump 28 connected between thermal focusing chamber 12 and separation column 20. Valve 52 controls the connection of vacuum pump 28 to the column and is preferably an electrically controlled valve or a pneumatically controlled valve which is shown being actuated by gas solenoid valve 54 through high pressure gas source 56. Interface unit 58 is used to control the operation of gas valve 54 through inputs from controller 40. It should be noted that these various elements which are used to control the flow of gases to vacuum pump 28 would be employed in conjunction with the first embodiment. However, in the prior description, valves 36 and 38 are shown in a simplified form for the sake of clarity. Gas chromatography system 50 incorporates a pair of pneumatic restrictors 60 and 62 which meet at a common junction which is connected to sample tube 14.

Figure 5:
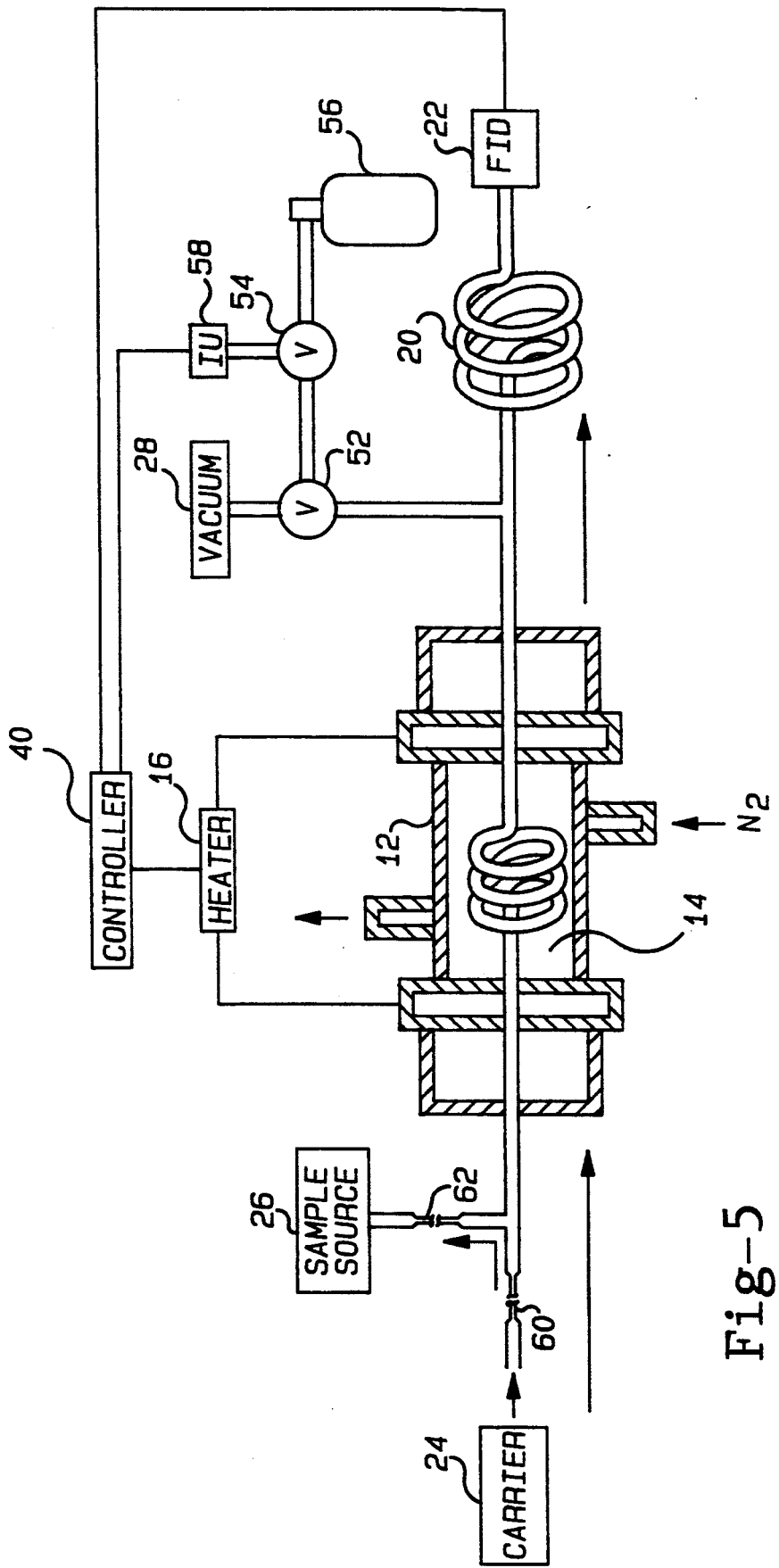
FIG. 5 is a schematic diagram similar to FIG. 4 except showing the direction of fluid flow during the injection mode of operation.

System 50 provides a unique inlet system which controls the introduction of a sample without the use of mechanical valves in the sample flow path. FIGS. 4 and 5 show such operation. In FIG. 4, arrows are provided showing the direction of fluid flow when the system is in a backflushing and trapping mode. In this mode, vacuum pump 28 is the lowest pressure point of the system and accordingly, all flow paths are directed toward it. Since the carrier gas is provided by source 24 at a positive pressure, flow of carrier gas occurs through restrictor 60. Simultaneously, a sample is drawn through restrictor 62. The sample becomes condensed within sample tube 14 which, in this mode, is maintained at a low temperature. Moreover, during this mode, column 20 is being backflushed due to a reverse flow through detector 22 and column 20. FIG. 5 is a simplified view like FIG. 4 except showing the direction of fluid flow when valve 52 is closed thus cutting off the vacuum exposure to column 20. In this mode, the lowest pressure point is at detector 22 and, therefore, the carrier gas flow occurs from the inlet point through restrictor 60 and ultimately through column 20. In this mode, a heating pulse would be applied by heater circuit 16 to inject a collected sample onto column 20. In this mode of operation, restrictor 62 is being backflushed and thus no new sample is being introduced.

As is evident from the foregoing description of gas chromatography system 50, the introduction of a sample is entirely controlled through control over vacuum pump 28. No valves are necessary in the inlet system. Moreover, the inlet conduit is automatically backflushed and thus purged during the injection mode upon every cycle of operation.

In an experimental prototype of system 50, a column 20 having a length of 150 cm. with a 0.25 mm. i.d. was used. The stationary phase was the same as the first embodiment. Restrictor 60 comprises a 33 cm. long, 0.1 mm. i.d. deactivated silica capillary and restrictor 62 comprised of a combination of a 33 cm. long 0.1 mm. i.d. and a 7 cm. long 0.1 mm. i.d. deactivated silica capillary. All other specifications for system 50 were identical to those of system 10.

While the above description constitutes the preferred embodiments of the present invention, it will be appreciated that the invention is susceptible of modification, variation and change without departing from the proper scope and fair meaning of the accompanying claims.

We claim:

1. A gas chromatography system comprising:
a source of a sample,
a source of a carrier gas,
a chromatography separation column,
a sample tube having a first end communicating with said source of a carrier gas and having a second end communicating with said column and said source of a sample,
temperature control means for controlling the temperature of said sample tube between a low temperature for condensing at least some components of said sample, and a high temperature for vaporizing said components,
a controllable pressure means for causing said sample to flow into said sample tube second end,
control means for controlling said temperature control means and said pressure means wherein during a collection mode, said pressure means draws said sample into said sample tube second end while said sample tube is at said low temperature, and during an injection mode, causes said sample tube to be heated to said high temperature and allowing said carrier gas to flow into said sample tube first end, through said sample tube, and into said column.

2. A gas chromatography system according to claim 1 wherein said controllable pressure means comprises a vacuum source communicating with said sample tube first end.

3. A gas chromatography system according to claim 2 further comprising a first conduit branch communicating said source of carrier gas with said sample tube first end, and a second conduit branch communicating said source of a sample with said sample tube second end, with first valve means between said first and second branches for allowing fluid flow between said branches, wherein during said collection mode, said first valve means is closed causing said carrier gas to flow through said first branch and to said vacuum source, and said sample to flow through said second branch and through said sample tube toward said vacuum source.

4. A gas chromatography system according to claim 3 wherein during said injection mode, said first valve means is opened allowing said carrier gas to flow through at least a portion of said second branch thereby flushing said portion.

5. A gas chromatography system according to claim 3 wherein said control means further controls said gas chromatography system to provide a backflush mode in which said source of vacuum is actuated and said first valve means is opened allowing said column and said second conduit branch to be purged.

6. A gas chromatography system according to claim 3 further comprising a first fluid restrictor means in said second branch between said first valve means and said sample source and a second fluid restrictor means in said second branch between said first valve means and said column, wherein said restrictors control the flow of fluids during said modes of operation.

7. A gas chromatography system according to claim 3 further comprising a third fluid restrictor means in said first conduit branch between said first valve means and said sample tube for controlling the flow of fluids during said modes of operation.

8. A gas chromatography system according to claim 3 wherein said vacuum source comprises a vacuum pump and a second valve means.

9. A gas chromatography system comprising:
a source of a sample,
a source of a carrier gas,
a chromatography separation column,
a sample tube,
temperature control means for controlling the temperature of said sample tube between a low temperature for condensing at least some components of said sample, and a high temperature for vaporizing said components, and
fluid circuit and control means for causing said sample to flow into said sample tube in a first direction of flow during a collection mode during which said sample tube is at said low temperature and causing said carrier gas to flow through said sample tube in an opposite second direction during an injection mode, during which said sample tube is at said high temperature.

10. A gas chromatography system according to claim 9 wherein said fluid circuit and control means comprises said sample tube having a first end communicating with said source of a carrier gas and having a second end communicating with said column.

11. A gas chromatography system according to claim 10 further comprising a controllable pressure means for causing said sample to flow into said tube second end in said first direction during said collection mode.

12. A gas chromatography system according to claim 11 wherein said controllable pressure means comprises a vacuum source communicating with said sample tube first end.

13. A gas chromatography system according to claim 12 further comprising a first conduit branch communicating said source of carrier gas with said sample tube first end, and a second conduit branch communicating said source of a sample to said sample tube second end, with first valve means between said first and second branches for allowing fluid flow between said branches, wherein during said collection mode, said first valve means is closed causing said carrier gas to flow through said first branch and toward said vacuum source, and said sample to flow through said second branch and through said sample tube in said first direction toward said vacuum source.

14. A gas chromatography system according to claim 13 wherein during said injection mode, said first valve means is opened allowing said carrier gas to flow through at least a portion of said second branch thereby flushing said portion.

15. Gas chromatography system according to claim 13 further comprising a first fluid restrictor means in said second branch between said first valve means and said sample source and a second fluid restrictor means in said second branch between said first valve means and said column, wherein said restrictors control the flow of fluids during said modes of operation.

16. A gas chromatography system according to claim 13 further comprising a third restrictor means in said first conduit branch between said first valve means and said sample tube, for controlling the flow of fluids during said modes of operation.

17. A gas chromatography system according to claim 12 wherein said control means further controls said gas chromatography system to provide a backflush mode in which said source of vacuum is actuated and said first valve means is opened allowing said column and said second conduit branch to be purged.

18. A gas chromatography system according to claim 12 wherein said vacuum source comprises a vacuum pump and a second valve means.

19. A gas chromatography system comprising:
a source of a sample,
a source of a carrier gas
a chromatography separation column,
a sample tube in fluid communication with said column having an inlet end and an outlet end,
a temperature control means for controlling the temperature of said sample tube between a low temperature for condensing at least some components of said sample, and a high temperature for vaporizing said components,
a controllable source of vacuum communicating between said sample tube and said column,
first restrictor means communicating with said carrier gas source and to said sample tube first end,
second restrictor means communicating said sample source with said sample tube first end, and
control means for providing a collection mode energizing said vacuum source for drawing said carrier gas and said sample source through said restrictors into said sample tube while said sample tube is at said low temperature, and in an injection mode deactivating said vacuum source causing said carrier gas to purge said second restrictor and injecting said sample into said column as said sample tube is at said high temperature.

20. A gas chromatography system according to claim 19 wherein said sample source comprises ambient air.

* * * * *

UNITED STATES PATENT AND TRADEMARK OFFICE
CERTIFICATE OF CORRECTION

PATENT NO. : 5,141,534

DATED : Aug. 25, 1992

INVENTOR(S) : Sacks et al.

Page 1 of 5

It is certified that error appears in the above-indentified patent and that said Letters Patent is hereby corrected as shown below:

The title page should be deleted and substitute therefor the attached title page.

Figs. 1, 2, and 3 should be deleted and the attached Figs. 1, 2, and 3 should be substituted therefor as shown on the attached pages.

Signed and Sealed this

Twenty-sixth Day of April, 1994

Attest:

BRUCE LEHMAN

*Attesting Officer*  *Commissioner of Patents and Trademarks*

United States Patent [19]
Sacks et al.

[11] Patent Number: 5,141,534
[45] Date of Patent: Aug. 25, 1992

[54] SAMPLE COLLECTION AND INLET SYSTEMS FOR GAS CHROMATOGRAPHY APPARATUS

[75] Inventors: Richard D. Sacks; Mark A. Klemp; Christine L. Rankin, all of Ann Arbor, Mich.

[73] Assignee: The Regents of the University of Michigan, Ann Arbor, Mich.

[21] Appl. No.: 717,356

[22] Filed: Jun. 18, 1991

Related U.S. Application Data

[63] Continuation-in-part of Ser. No. 590,174, Sep. 28, 1990, Pat. No. 5,096,471.

[51] Int. Cl.$^5$ .................................. B01D 15/08
[52] U.S. Cl. ........................... 55/197; 55/267; 55/386
[58] Field of Search ............ 55/67, 197, 208, 267, 55/269, 386

[56] References Cited

U.S. PATENT DOCUMENTS

| | | | |
|---|---|---|---|
| 3,111,835 | 11/1963 | Jenkins | 73/23 |
| 3,220,164 | 11/1965 | Golay | 73/23.42 X |
| 3,496,702 | 2/1970 | Carel et al. | 55/67 |
| 3,550,428 | 12/1970 | Mator et al. | 73/23.36 |
| 3,735,565 | 5/1973 | Gilby et al. | 55/197 |
| 3,948,602 | 4/1976 | Solomon | 55/67 X |
| 4,035,168 | 7/1977 | Jennings | 55/197 X |
| 4,038,053 | 7/1977 | Gday | 55/67 X |
| 4,477,266 | 10/1984 | Yang et al. | 55/67 |
| 4,805,441 | 2/1989 | Sides et al. | 73/23.1 |
| 4,863,871 | 9/1989 | Munari et al. | 436/161 |
| 4,923,486 | 5/1990 | Rubey | 55/67 |
| 4,962,042 | 10/1990 | Morabito et al. | 55/197 X |

OTHER PUBLICATIONS

"Sample Enrichment in High Speed Narrow Bore Capillary Gas Chromatography", Van Es et al., J. of High Resolution Chrom. & Chrom. Communications, vol. 11, Dec. 1988, pp. 852-857.
"Rapid Evaporation of Condensed Gas Chromatographic Fractions", Hopkins et al., J. of Chromatography, 158 (1978) 465-469.
B. A. Ewels and R. D. Sacks, 1985, "Electrically Heated Cold Trap Inlet System for High-Speed Gas Chromatography", Analytical Chemistry, 57, 2774-2779.
Lanning, Sacks, Mouradian, Levine, Foulke, "Electrically Heated Cold Trap Inlet System for Computer-Controlled Controlled High-Speed Gas Chromatography", Anal. Chem. 1988, 60, 1994-1996.
S. Levine, R. Sacks, Jul. 1, 1986-Jun. 30, 1988, "Fast-GC for Industrial Hygiene Monitoring/Analysis", U. of Michigan, Grant No. 86-363-J1.

*Primary Examiner*—Robert Spitzer
*Attorney, Agent, or Firm*—Harness, Dickey & Pierce

[57] ABSTRACT

A gas chromatography system of the type incorporating a thermal focusing chamber for introducing a sample into a column for separation and analysis. The system of the present invention provides benefits in terms of reducing memory effect of one analysis being influenced by prior experiments, a reduction in system dead volume which leads to broadening of peaks produced on the chromatogram and artifacts caused by sample decomposition. These advantages are achieved principally through a novel fluid circuit in which the sample is trapped onto the column by trapping it at the end of the thermal focusing chamber closest to the column. This feature has the effect of eliminating the necessity of the sample residing in the heated focusing chamber for a period giving rise to sample decomposition. This system further avoids the necessity of passing the inlet flow through mechanical valves which also contributes to memory effect. This system further has the benefit of enabling sampling of sources at various pressures including ambient pressure as an air quality sensing probe. An alternative embodiment is a simplified system for enabling ambient pressure source monitoring without mechanical valves in the sample flow path.

20 Claims, 4 Drawing Sheets

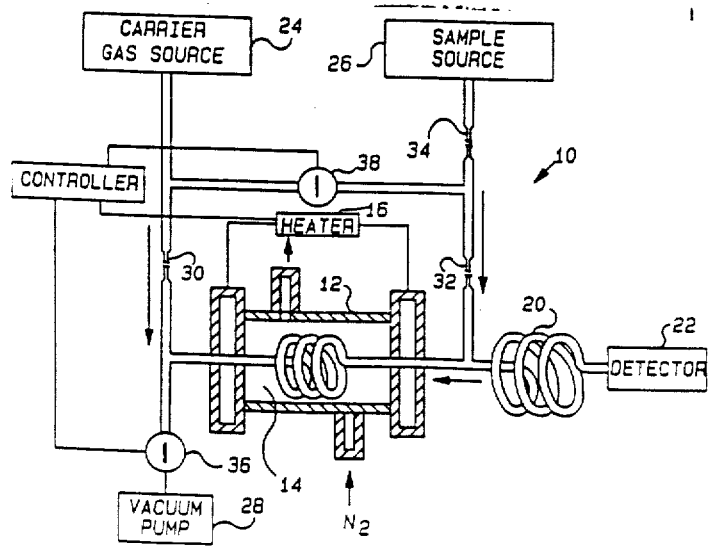

UNITED STATES PATENT AND TRADEMARK OFFICE
CERTIFICATE OF CORRECTION

PATENT NO. : 5,141,534

DATED : August 25, 1992

INVENTOR(S) : Richard D. Sacks, Mark A. Klemp, Christine L. Rankin

It is certified that error appears in the above-identified patent and that said Letters Patent is hereby corrected as shown below:

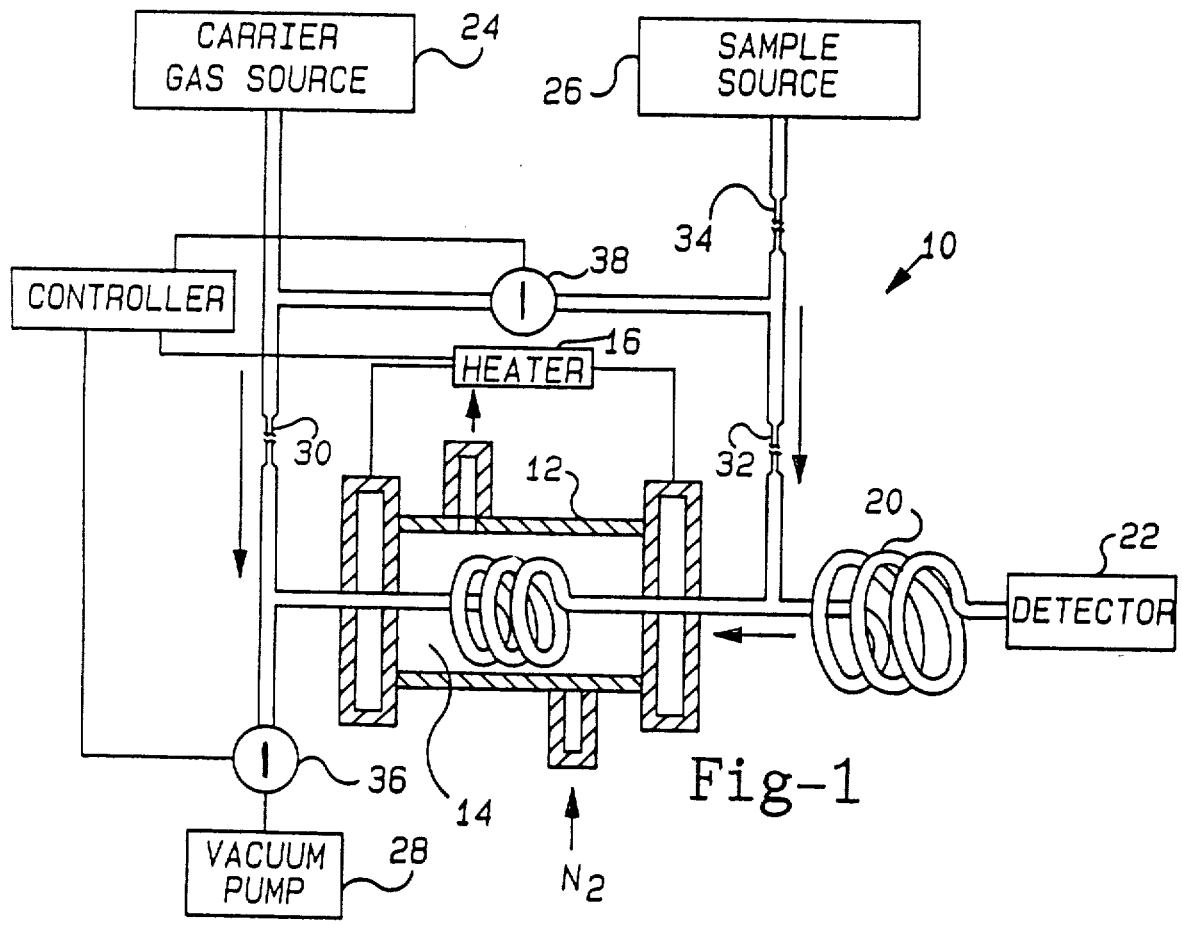

Fig-1

UNITED STATES PATENT AND TRADEMARK OFFICE
CERTIFICATE OF CORRECTION

PATENT NO. : 5,141,534

DATED : August 25, 1992

INVENTOR(S) : Richard D. Sacks, Mark A. Klemp, Christine L. Rankin

It is certified that error appears in the above-identified patent and that said Letters Patent is hereby corrected as shown below:

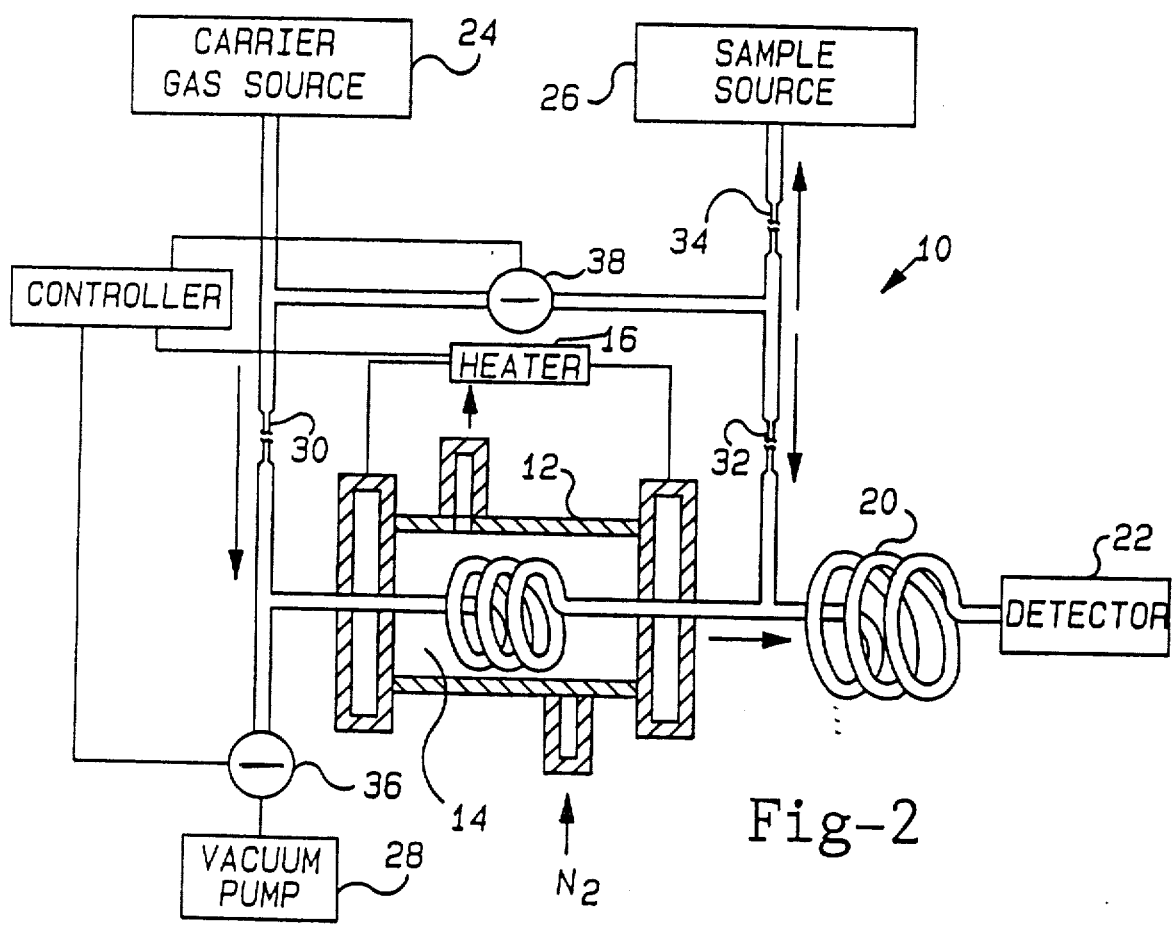

Fig-2

UNITED STATES PATENT AND TRADEMARK OFFICE
CERTIFICATE OF CORRECTION

PATENT NO. : 5,141,534

DATED : August 25, 1992

INVENTOR(S) : Richard D. Sacks, Mark A. Klemp, Christine L. Rankin

It is certified that error appears in the above-identified patent and that said Letters Patent is hereby corrected as shown below:

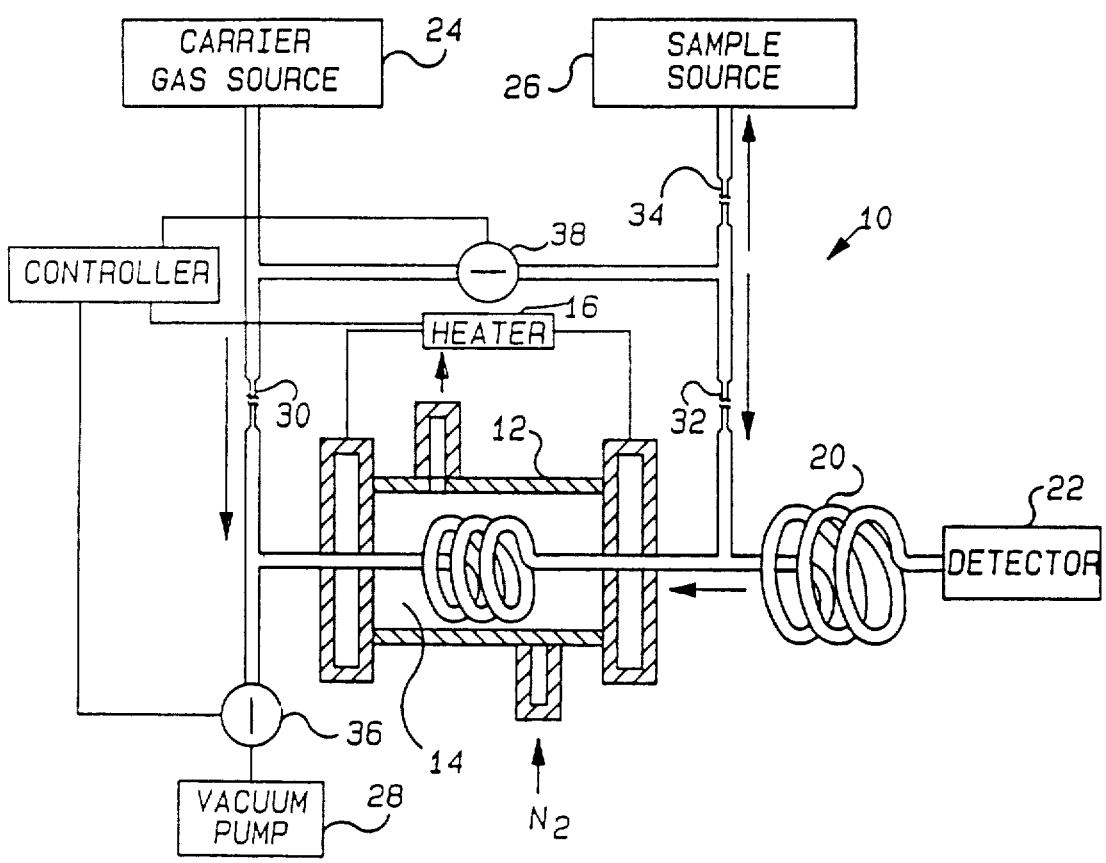

Fig-3